(12) United States Patent
Pratt et al.

(10) Patent No.: US 8,883,127 B2
(45) Date of Patent: Nov. 11, 2014

(54) BLEACHING/HIGHLIGHTING COMPOSITION CONTAINING CALCIUM SALTS

(75) Inventors: Dominic Pratt, Buettelborn (DE); Sabine Thieme, Ruesselsheim (DE)

(73) Assignee: Kao Germany GmbH, Darmstadt (DE)

( * ) Notice: Subject to any disclaimer, the term of this patent is extended or adjusted under 35 U.S.C. 154(b) by 111 days.

(21) Appl. No.: 12/867,080

(22) PCT Filed: Mar. 2, 2009

(86) PCT No.: PCT/EP2009/001459
§ 371 (c)(1), (2), (4) Date: Sep. 20, 2010

(87) PCT Pub. No.: WO2009/109345
PCT Pub. Date: Sep. 11, 2009

(65) Prior Publication Data
US 2011/0052518 A1  Mar. 3, 2011

(30) Foreign Application Priority Data

Mar. 4, 2008 (EP) .................................. 08003950

(51) Int. Cl.
| | | |
|---|---|---|
| *A61K 8/25* | (2006.01) | |
| *A61Q 5/08* | (2006.01) | |
| *A61K 8/19* | (2006.01) | |
| *A61K 8/21* | (2006.01) | |
| *A61K 8/22* | (2006.01) | |
| *A61K 8/23* | (2006.01) | |
| *A61K 8/24* | (2006.01) | |
| *A61K 8/26* | (2006.01) | |
| *A61K 8/36* | (2006.01) | |
| *A61K 8/365* | (2006.01) | |
| *A61K 8/368* | (2006.01) | |
| *A61K 8/44* | (2006.01) | |
| *A61Q 5/10* | (2006.01) | |

(52) U.S. Cl.
CPC ... *A61Q 5/08* (2013.01); *A61K 8/19* (2013.01); *A61K 8/21* (2013.01); *A61K 8/22* (2013.01); *A61K 8/23* (2013.01); *A61K 8/24* (2013.01); *A61K 8/25* (2013.01); *A61K 8/26* (2013.01); *A61K 8/36* (2013.01); *A61K 8/365* (2013.01); *A61K 8/368* (2013.01); *A61K 8/44* (2013.01); *A61Q 5/10* (2013.01); *A61K 2800/4322* (2013.01)
USPC ..................................... 424/62; 8/405; 8/406

(58) Field of Classification Search
USPC ......................................... 424/62; 8/405, 406
See application file for complete search history.

(56) References Cited

U.S. PATENT DOCUMENTS

| | | | |
|---|---|---|---|
| 2,554,464 A | | 5/1951 | Kraus |
| 2004/0022823 A1 * | | 2/2004 | Uchida et al. .................. 424/401 |
| 2004/0170590 A1 * | | 9/2004 | Fahnestock et al. ........ 424/70.14 |
| 2006/0269492 A1 | | 11/2006 | Narasimhan |

FOREIGN PATENT DOCUMENTS

| | | | | |
|---|---|---|---|---|
| GB | 859276 | * | 2/1958 | |
| GB | 859276 | * | 1/1961 | |
| GB | 859276 A | | 1/1961 | |
| JP | 2003206221 A | | 7/2003 | |
| JP | 2008-225354 | * | 8/2006 | ............... A61K 8/00 |
| WO | 2007/025750 A | | 3/2007 | |

OTHER PUBLICATIONS

International Search Report Dated May 15, 2009.

* cited by examiner

*Primary Examiner* — Anoop Singh
*Assistant Examiner* — Anna Falkowitz
(74) *Attorney, Agent, or Firm* — Norris McLaughlin & Marcus PA

(57) ABSTRACT

The present invention relates to bleaching composition for keratin fibres, especially human hair, comprising at least one compound with bleaching and/or highlighting effect and a calcium salt. Further object of the present invention is the use of at least one calcium salt in a bleaching and/or highlighting composition for keratin fibres, especially for human hair, comprising at least one compound with bleaching and/or highlighting effect for preventing temperature increase going above 40° C., preferably above 45° C. and more preferably above 50° C. in a period of at least 60 min after mixing water free bleaching and/or highlighting composition and oxidizing lotion.

12 Claims, 1 Drawing Sheet

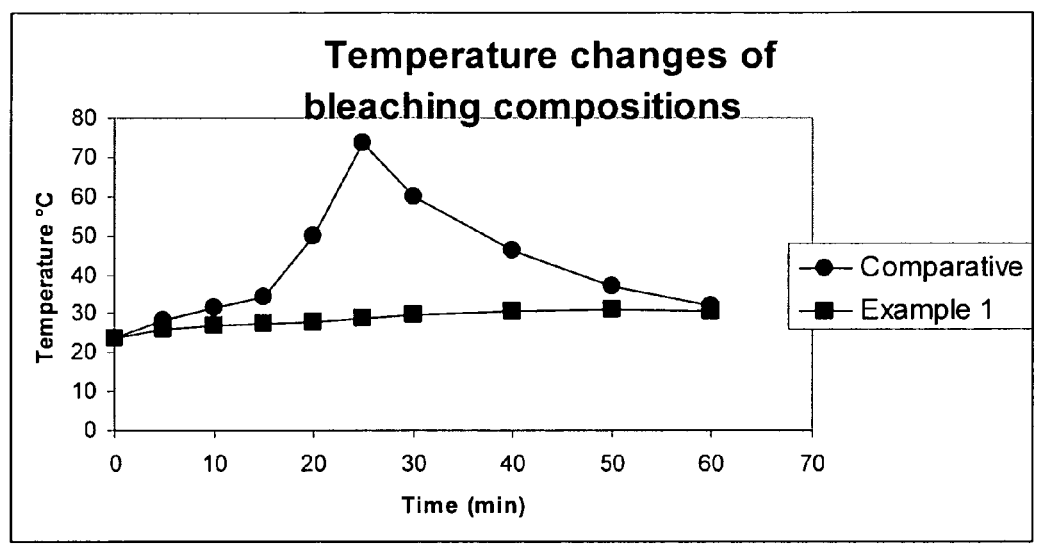

BLEACHING/HIGHLIGHTING COMPOSITION CONTAINING CALCIUM SALTS

This application is a 371 application of PCT/EP2009/001459 filed Mar. 2, 2009, which claims priority to the EP application 08003950.6 filed Mar. 4, 2008.

The present invention relates to bleaching composition for keratin fibres, especially human hair, comprising at least one compound with bleaching and/or highlighting effect and a calcium salt.

Hair bleaching is a common practice for ages. It is based on oxidative decomposition of hair colour, which is usually done using peroxide or peroxide releasing compounds such as persulfates. Due to highly irritating potential of these bleaching ingredients and dustiness of powder compositions, it is preferred to provide granular composition where dust is reduced by agglomerating small particles into granulates using various binding agents. Most popular binding agent is mineral oil, which was the subject matter of EP 560 088 B1. Furthermore, EP 778 020 A1 suggests the use of oil and wax compounds or their mixtures for preparation of suspensions.

The bleaching of human hair customarily consists of a process with the following steps: Homogenous mixing of a water-free preparation, preferably a powder, comprising at least one compound with a bleaching and/or highlighting effect, in particular a solid peroxide salt, preferably ammonium, potassium and/or sodium persulfate or earth alkali peroxide, with an aqueous hydrogen peroxide composition, application of this composition onto the hair, and rinsing after bleaching is completed. It has been known for some time that use of these compounds is effective with regard to the bleaching, but higher concentrations can lead to hair damage and/or scalp irritation. In some cases, it has further been observed that during mixing of the above mentioned two compositions and/or processing on the hair after application of the mixture, excessive heat develops which results in excessive hair damage and extreme scalp irritations and more seriously scalp burning. It was found out that in some cases temperature on the hair and scalp raises easily to approximately 80° C. Prevention of said excessive heat development will help very much to a safe and milder beaching process.

The source of the excessive heat development can be any reaction taking place within the mixture of aqueous oxidizing and water free bleaching compositions. Without being bound by the theory, it has been thought that heavy metal ion contaminations can be responsible for extreme and steady increase in the temperature of the mixture either during mixing or during processing on keratin fibre especially hair. Heavy metal ions may be introduced to the mixture by non-optimal working conditions such as using improperly cleaned utensils and also by the use of contaminated water for cleaning the equipment used for mixing and applying bleaching composition onto hair. Another source may be deposition of heavy metals on or into hair from the environment.

In order to test the above theory, cupper chloride was added into the mixture of bleaching powder and oxidizing lotion and the temperature of the mixture was observed for a period of 60 min. It was found out that at the beginning temperature increase is rather slow but after a period of 15 min a rapid increase was found. The highest temperature reached was approximately 75° C. (FIG. 1)

Therefore, aim of the present invention is to find out a composition for bleaching and/or highlighting hair with which such excessive heat development does not take place.

The inventors of the present invention have surprisingly found out that excessive heat development does not take place when a calcium salt (see below for the specific calcium salts referred to) is used in water free bleaching composition which is than mixed with an oxidizing composition.

Use of various calcium salts is know from a Japanese patent publication JP 2003-206221 A1 for enhancing bleaching effect. In the document calcium chloride, iodide and bromide salts have been mentioned. The document does not address excessive heat development and/or prevention of it.

The first object of the present invention is a water free bleaching and/or highlighting composition for keratin fibres, especially human hair, comprising at least one compound with bleaching and/or highlighting effect and at least one calcium salt selected from calcium aluminium borosilicate, calcium aspartate, calcium benzoate, calcium acetate, calcium carbonate, calcium citrate, calcium dihydrogen phosphate, calcium fluoride, calcium hydroxide, calcium lactate, calcium monofluorophosphate, calcium oxide, calcium phosphate, calcium propionate, calcium pyrophosphate, calcium sulphate, calcium nitrate, calcium salicylate, calcium silicate, hydrate, calcium tartarate, tricalcium phosphate.

The second object of the present invention is the use of at least one calcium salt in a bleaching composition for keratin fibres, especially for human hair, comprising at least one compound with bleaching and/or highlighting effect for preventing excessive heat development.

The third object of the present invention is the use of at least one calcium salt in a bleaching and/or highlighting composition for keratin fibres, especially for human hair, comprising at least one compound with bleaching and/or highlighting effect for preventing temperature increase going above 40° C., preferably above 45° C. and more preferably above 50° C. in a period of at least 60 min after mixing water free bleaching and/or highlighting composition and oxidizing lotion.

With the term "excessive heat development" it is meant that the temperature of the bleaching composition is being above 40° C., preferably above 45° C., more preferably above 50° C. after mixing water free composition comprising at least compound with bleaching and/or highlighting effect and at least one calcium salt referred above and a composition comprising at least one oxidizing agent at a time within 60min.

The term bleaching composition is used to define any bleaching composition either water free or an aqueous i.e. after mixing with aqueous oxidizing agent.

With the term "water free bleaching and/or highlighting composition" it is meant that no additional water is introduced into the composition other than bound water to the ingredients which may be as high as 1% of the composition.

Bleaching and/or highlighting compositions of the present invention comprises at least one calcium salt. Both organic and inorganic ones are suitable for the purpose of the present invention. Inorganic salts are most preferred. Suitable calcium salts are calcium aluminium borosilicate, calcium aspartate, calcium benzoate, calcium acetate, calcium carbonate, calcium citrate, calcium dihydrogen phosphate, calcium fluoride, calcium hydroxide, calcium lactate, calcium monofluorophosphate, calcium oxide, calcium phosphate, calcium propionate, calcium pyrophosphate, calcium sulphate, calcium nitrate, calcium salicylate, calcium silicate, hydrate, calcium tartarate, tricalcium phosphate, calcium chloride, calcium iodide and calcium bromide. Preferred are calcium benzoate, calcium acetate, calcium carbonate, calcium citrate, calcium dihydrogen phosphate, calcium fluoride, calcium hydroxide, calcium lactate, calcium monofluorophosphate, calcium oxide, calcium phosphate, calcium propionate, calcium pyrophosphate, calcium sulphate, calcium nitrate, calcium salicylate, calcium silicate, hydrate, calcium tartarate, tricalcium phosphate, calcium chloride, calcium iodide and calcium bromide. More preferred calcium acetate, calcium carbonate, calcium citrate, calcium dihydrogen phosphate, calcium fluoride, calcium hydroxide, calcium lactate, calcium oxide, calcium phosphate, calcium propionate, calcium pyrophosphate, calcium sulphate, calcium nitrate, calcium silicate, calcium tartarate, calcium chloride, calcium iodide and calcium bromide. The most preferred are calcium carbonate, calcium dihydrogen phosphate, calcium fluoride, calcium hydroxide, calcium oxide, calcium phosphate, calcium pyrophosphate, calcium sulphate, calcium nitrate, calcium chloride, calcium iodide and calcium bromide. Calcium sulphate is particularly preferred because of its outstanding effect.

Concerning the above mentioned list of calcium salts it should be noted that calcium chloride, calcium iodide and calcium bromide are inserted into the list because of their use for preventing the excessive heat development because Japanese patent publication mentioned above discloses the three calcium salt in a bleaching composition.

Concentration of at least one calcium salt in the compositions of the present invention is between 0.1 and 20%, preferably between 0.5 and 15%, more preferably between 0.75 and 10% and most preferably between 1 and 7.5% by weight calculated to total composition prior to mixing with oxidizing lotion.

According to the present invention, the composition comprises at least one compound with bleaching and/or highlighting effect. Suitable compounds are in general peroxides. Useful as such are in particular persulfates such as sodium and potassium persulfate, ammonium persulfate, earth alkali peroxides such as magnesium peroxide, melamine peroxide or urea peroxide or phtholimidoperoxy-hexanoic acid, and mixtures thereof. The proportion of peroxides is at least 5%, preferably in the range of 20 to 80%, more preferably 25 to 60% and most preferably 30 to 55% by weight, calculated to total composition prior to mixing with oxidizing lotion.

According to the invention, the water free composition can also comprise 0.1% to 10% by weight, calculated to total composition prior to mixing with oxidizing lotion, at least one ammonium salts. Suitable ammonium salts are ammonium carbonate, ammonium hydrogen carbonate, ammonium carbamate, ammonium chloride, ammonium sulfate, ammonium phosphates, ammonium nitrate, ammonium bromide, ammonium iodide, ammonium thiosulfate, ammonium molybdate, ammonium vanadate, ammonium sulfamate, ammonium citrate, ammonium salicylate, ammonium valerate, ammonium tartarate, ammonium benzoate, ammonium acetate, ammonium formiate and ammonium lactate. Compositions may also comprise mixture or ammonium salts.

Preferred thereof are the ammonium phosphates, such as ammonium dihydrogen phosphate, ammonium hydrogen phosphate, diammonium sodium phosphate, sodium ammonium hydrogen phospahe, ammonium disodium phosphate, as well as ammonium chloride, ammonium sulphate, diammonium hydrogen citrate, ammonium carbonate, ammonium hydrogen carbonate preferably in an amount from 0.1% to 10% by weight, calculated to total composition prior to mixing with oxidizing lotion.

As known from EP 609 796 A2, the ammonium compounds can also be used as sole bleaching agent in respectively higher amounts.

The total proportion of the compounds with bleaching and/or highlighting effect preferably ranges from 5% to 85%, preferably 20% to 80%, more preferably 25 to 70% and most preferably 30 to 60% by weight calculated to total composition prior to mixing with oxidizing lotion.

In addition to the active component, water free bleaching and/or highlighting compositions also comprise the components customarily used in such compositions: In particular inert pulverulent carrier materials, these are for example, pyrogenic silicium dioxide, starch powder, etc., alkalizing agents, such as sodium metasilicate, surface-active substances, binding agents, etc. In order to avoid repetition, reference is made to the respective standard literature, for example, K. Schrader and A. Domsch, "Cosmetology—Theory and Practice (2005, Verlag fur Chemische Industrie), pages 142 to 151.

In a preferred embodiment of the present invention, water free bleaching and highlighting composition of the present invention is in powder form and in particular in dust free powder form and comprises oily lipophilic ingredients such as vegetable oils, for example, jojoba oil or any other; petrolatum liquid paraffins, especially paraffinum perliquidum and parafiinum subliquidum; silicone oils; hydropobic fatty acid esters such as octyl palmitate, isocetyl palmitate, isopropyl palmitate and octyl stearate, $C_{10}$- to $C_{36}$-fatty acid triglycerides, as well as their mixtures. In the case that the use is wished among those the most preferred ones are silicone oils, jojoba oil, fatty acid esters, paraffin oils, combinations of fatty acid esters and paraffin oils. Fatty acid esters and/or paraffin oils and/or silicone oils are particularly preferred. Concentration of these oily lipophilic compounds are used in a total amount of about 0.1 to 50% by weight, preferably from 1 to 40% by weight, and more preferably from 2 to 35% by weight, calculated to total composition prior to mixing with oxidizing lotion.

In principal any silicone oil is useful as a lipophilic compound. Preferred are dimthicones, dimethiconols and arylated silicones as a lipophilic ingredient at a concentration range of 0.1 to 50%, preferably 0.5 to 40% more preferably 1 to 35% and most preferably 2.5 to 30% by weight calculated to total composition prior to mixing with oxidizing lotion. Non-limiting suitable examples are dimethicones with various viscosity available from Dow Corning under the trade name DC 200, arylated silicones such as phenyl methicone, phenyl trimethicone, diphenyl dimethicone, diphenylsiloxy phenyl trimethicone, tetramethyl tetraphenyl trisiloxane, triphenyl trimethicone, tetramethly tetraphenyl trisiloxane and pentaphenyl trimethyl trisiloxane.

Further, in another preferred form of the invention water free composition for bleaching and/or highlighting hair comprises polymers from the group consisting of cellulose polymer compounds, alginate, polysaccarides and acrylic acid polymers, preferably methyl cellulose compounds, ethyl cellulose compounds, hydroxyethylcellulose compounds, methylhydroxyethylcellulose compounds, methylhydroxypropylcellulose compounds, carboxymethyl cellulose compounds, alginic acids, sodium alginates, ammonium alginates, calcium alginates, gum arabic, guar gum or xanthan gum, or acrylic acid polymers with molecular weights from about 1,250,000 to 4,000,000, alone or in combination with each other. The polymers are used in a total amount of 0.1 to 15%, preferably from 0.2 to 10%, and more preferably in an amount of from 0.5 to 7.5% by weight, calculated to total composition prior to mixing with oxidizing lotion.

Water free bleaching and/or highlighting composition can also comprise cationic polymers as conditioning and/or thickening agents. Those are cationic cellulose type polymers know as Polymer JR type from Amerchol such as Polyquaternium 10 or cationic guar gum known with trade name Jaguar from Rhône-Poulenc and chemically for example Guar hydroxypropyl trimonium chloride. Furthermore, chitosan and chitin can also be included in the compositions as cationic natural polymers.

Furthermore, it has been found suitable those cationic polymers known with their CTFA category name Polyquaternium. Typical examples of those Polyquaternium 1, Polyquaternium 2, Polyquaternium 4, Polyquaternium 5, Polyquaternium 6, Polyquaternium 7, Polyquaternium 8, Polyquaternium 9, Polyquaternium 10, Polyquaternium 11, Polyquaternium 12, Polyquaternium 13, Polyquaternium 14, Polyquaternium 15, Polyquaternium 16, Polyquaternium 17, Polyquaternium 18, Polyquaternium 19, Polyquaternium 20, Polyquaternium 22, Polyquaternium 24, Polyquaternium 27, Polyquaternium 28, Polyquaternium 29, Polyquaternium 30, Polyquaternium 31, Polyquaternium 32, Polyquaternium 33, Polyquaternium 34, Polyquaternium 35 and Polyquaternium 36, Polyquaternium-37, Polyquaternium 39, Polyquaternium 42, Polyquaternium 43, Polyquaternium 44, Polyquaternium 45, Polyquaternium 46, Polyquaternium 47, Polyquaternium 48, Polyquaternium-49, Polyquaternium 50, Polyquaternium 51, Polyquaternium 52, Polyquaternium 53, Polyquaternium 54, Polyquaternium 55, Polyquaternium 56, Polyquaternium 57, Polyquaternium 58, Polyquaternium 59, Polyquaternium 60, Polyquaternium 61, Polyquaternium 62, Polyquaternium 63, Polyquaternium 64, Polyquaternium 65, Polyquaternium 66, Polyquaternium 67, Polyquaternium 68, Polyquaternium 69, Polyquaternium-70, Polyquaternium 71, Polyquaternium 72, Polyquaternium 73, Polyquaternium 74, Polyquaternium 75, Polyquaternium 76, Polyquaternium 77, Polyquaternium 78, Polyquaternium-79, Polyquaternium 80, Polyquaternium 81, Polyquaternium 82, Polyquaternium 83, Polyquaternium 84, Polyquaternium 85, Polyquaternium 86 and Polyquaternium 87.

As well those polymers known with their CTFA category name Quaternium are suitable. Those are for example Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-82, Quaternium-83 and Quaternium-84.

Typical concentration range for any of the cationic conditioners mentioned above can be 0.1-7.5% by weight, preferably 0.3-5% by weight and more preferably 0.5-2.5% by weight, calculated to total composition prior to mixing with an oxidizing agent.

Water free bleaching and/or highlighting composition of the present invention may comprise at least one dialkyl carbonate of general formula

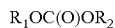

where $R_1$ and $R_2$ are independent from each other linear or branched saturated alkyl chains with 6 to 22 C atoms.

Preferred at least one dialkyl carbonate is selected from di(caprylyl) carbonate and di(ethylhexyl) carbonate.

Concentration of at least dialkyl carbonate may vary between 0.1 and 30% by weight calculated to total composition prior to mixing with an oxidizing agent.

Water free bleaching and/or highlighting compositions of the present invention can comprise synthetic mica coated with metal oxide or oxides having a volume particle size distribution in the range of 1 to 750 µm. Use of synthetic mica coated with metal oxide or oxides mainly in decorative cosmetics is disclosed in an international patent application of Sun Chemical Corporation published with a number WO 2005/065632 A1. In the document synthetic mica and coated synthetic mica with at least one metal oxide or oxides is disclosed in detail. The content of the document is included herewith by reference.

Suitable metal oxide or oxides for coating synthetic mica are titanium dioxide, chromium oxide, ferric oxide or mixtures thereof. In the present invention the preferred is synthetic mica coated with titanium dioxide. Such materials are commercially available from Sun Chemical Corporation and Merck (Timiron Synwhite 40) and known with their INCl names Synthetic Fluorphologopite The volume particle size distribution of synthetic mica coated with a metal oxide or oxides is in the range of 1 to 750 µm, preferably 1 to 250 µm, more preferably 1 to 100 µm and most preferably 5 to 95 µm. The particle sizes referred are relating to the volume particle size distribution meaning that particles found in the coated synthetic mica having volume particle size in the given ranges.

Concentration of synthetic mica coated with at least metal oxide or oxides is from 0.01 to 20%, preferably 0.1 to 15%, more preferably 0.25 to 10% and most preferably 0.5 to 55% by weight calculated to total composition prior to mixing with an oxidizing agent.

Interestingly, it has been observed that the mixture of water free powder composition comprising at least one bleaching and/or highlighting agent and synthetic mica coated with at least one metal oxide or oxides with a particle size as mentioned above and a composition comprising at least one oxidizing agent look very homogeneous, shiny and easy to apply onto hair than a mixture which does not comprise synthetic mica.

The average particle size of the dust free bleaching powder composition according to the invention is generally range below 1 mm, preferably below 500 µm, more preferably less than 400 µm and in particular about 25 to about 100 µm, thus ensuring excellent processing capability, i.e. miscibility with an aqueous hydrogen peroxide solution prior to application onto human hair.

The powder composition can be produced with processes such as by mixing the powdery ingredients first and subsequently adding lipophilic ingredient(s) and by fluidized bed method. In fluidized bed method, powder ingredients are mixed in a vessel and made flowing by inletting an air flow which may be heated (preferred when using waxy component) or carried out at room (ambient) temperature and while the powder mix freely "flowing" lipophilic ingredient and/or mixture with any other liquid component is sprayed from a nozzle mounted above the powder batch.

The bleaching and/or highlighting composition of the present invention is mixed prior to application with an oxidizing lotion comprising at least one oxidizing agent. The oxidizing agents suitable are hydrogen peroxide, urea peroxide, melamin peroxide or perborate salts. The most preferred is hydrogen peroxide. Such composition comprises 2 to 12% by weight at least one oxidizing agent preferably hydrogen peroxide and is either a solution or in the form of an emulsion. The mixing ratio is very much dependent on the level of bleaching effect targeted, i.e. the level of highlighting and/or bleaching and darkness of hair before bleaching, and can be adjusted accordingly by hair dressers. However, generally mixing ratio is within the range of 0.5 to 4 by weight (bleaching composition to oxidizing composition), preferably in the range of 1 to 2 by weight.

The pH of the ready to use product, mixture of bleaching composition and oxidizing lotion, is in the range of 8 to 12, in particular between 9 and 11.

In another preferred form of the present invention a third composition is mixed into the mixture of water free bleaching and/or highlighting composition and oxidizing composition. The third composition is preferably an aqueous composition and can be in form of a solution, thickened composition, gel, emulsion or a suspension. It may even be a product dispensed from a pressurised contained including any one of the above mentioned type of preparations.

The third composition preferably comprises at least one hair conditioning compound. Hair conditioning compound is preferably selected from non-ionic substances, oil or oily substances, cationic compounds.

Non-ionic conditioning agents can be polyethyleneglycol mono or di fatty acid esters having general formula

or

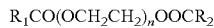

wherein $R_1$ and $R_2$ are independent from each other saturated, unsaturated or branched or non-branched alkyl chain with 7 to 21 C atoms and n is typically 2-100.

Suitable cationic conditioning compounds are those carrying a quaternary ammonium group or a cationizable group and selected from cationic polymers, cationic surfactants and quaternary ammonium or amino silicones. Suitable cationic polymers are those of best known with their CTFA category name Polyquaternium as disclosed above for water free bleaching and/or highlighting composition as well as those polymers known with their CTFA category name Quaternium and disclosed above for water free bleaching and/or highlighting composition.

The third composition and also water free bleaching composition of the present invention can comprise an organopolysiloxane wherein at least one silicium atom is linked to an alkylene group having a hetero-atom, in particular a nitrogen atom, with a poly-(N-acyl alkyleneimine) units of the formula

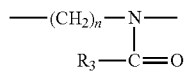

wherein n is a number from 1 to 5 and $R_3$ is hydrogen, a $C_1$-$C_{12}$-alkyl or cycloalkyl, aralkyl or aryl group as a conditioning agent. Preferred organopolysiloxane polymers are those of the type disclosed in EP-A 640 643, in particular optionally quaternized aminoalkyl, in particular aminopropyl dimethyl polysiloxane/polyethyl oxazoline copolymers of the formula

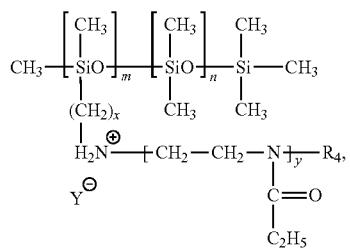

wherein m and n each are numbers from 20 to 10,000, in particular 50 to 7,000, especially 100 to 5,000, x is a number between 1 and 5, preferably 3, and y is a number from 5 to 30, $R_4$ is a $C_1$-$C_{12}$-alkyl or aryl group, in particular a methyl, ethyl or benzyl group, and Y⁻ is an anion.

Especially suited are the organopolysiloxanes disclosed under the terms A-1, A-2 and A-3 on pages 12 to 13 of EP-A 640 643. The proportion of graft copolymers in the hair colouring compositions according to the invention ranges from 0.05% to 5%, preferably 0.1% to 2.5%, in particular 0.5% to 1.5% by weight, calculated to the total composition prior to mixing with oxidizing and bleaching and/or highlighting composition.

Cationic surfactants suitable for the third composition of the present invention are according to the general formula

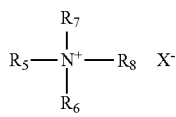

where $R_5$ is a saturated or unsaturated, branched or straight alkyl chain with 8-22 C atoms or

where $R_9$ is saturated or unsaturated, branched or straight alkyl chain with 7-21 C atoms and n has value of 1-4, or

where $R_{10}$ is saturated or unsaturated, branched or straight alkyl chain with 7-21 C atoms and n has value of 1-4, and $R_6$ is hydrogen or unsaturated or saturated, branched or straight alkyl chain with 1-22 C atoms or

or

where $R_9$, $R_{10}$ and n are same as above.

$R_7$ and $R_8$ are hydrogen or lower alkyl chain with 1 to 4 carbon atoms, and X is anion such as chloride, bromide, methosulfate.

Typical examples of those ingredients are cetyltrimethyl ammonium chloride, steartrimonium chloride, behentrimonium chloride, stearamidopropyl trimonuim chloride, dioleoylethyl dimethyl ammonium methosulfate, dioleoylethyl hydroxyethylmonium methosulfate.

Amido amines may as well be used as a conditioning cationic surfactant in the compositions of the present invention. Typical non-limiting example is stearamidopropylamine known with a trade name Tego Amid S18 from Degussa and behenamidopropyl dimethyl amine available under the trade name Amidet APA 22 from Kao Chemicals.

Oily substances are selected from such as silicone oils, volatile or non-volatile, natural and synthetic oils. Among silicone oils those can be added to the compositions include dimethicone, dimethiconol, polydimethylsiloxane, DC fluid ranges from Dow Corning, arylated silicones such as phenyl trimethicone or any other silicone with up to 5 aryl, preferably phenyl, group in its molecule, natural oils such as olive oil, almond oil, avocado oil, wheatgerm oil, ricinus oil and the synthetic oils, such as mineral oil, isopropyl myristate, palmitate, stearate and isostearate, oleyl oleate, isocetyl stearate, hexyl laurate, dibutyl adipate, dioctyl adipate, myristyl myristate and oleyl erucate.

The compositions according to the invention may also comprise further conditioning substances such as protein hydrolyzates and polypeptides, e.g., keratin hydrolyzates, collagen hydrolyzates of the type "Nutrilan$^R$" or elastin hydrolyzates, as well as also in particular plant protein hydrolyzates, optionally, cationized protein hydrolyzates, e.g., "Gluadin$^R$".

Typical concentration range for any of those conditioners, non-ionic compounds, oil or oil like substances, cationic polymers, silicon oil and derivatives and cationic surfactants is in the range of 0.01-10% by weight, preferably 0.01-7.5% by weight, more preferably 0.05-5% and most preferably 0.1-5% by weight calculated to the total composition prior to mixing with oxidizing and bleaching and/or highlighting composition.

In the case that the third composition is in the form of an emulsion, it comprises as an emulsion base at least one fatty alcohol or mixture of fatty alcohols with the chain length of 14 to 22 C atoms. Examples to suitable fatty alcohols, without limiting the choice, are myristyl alcohol, cetyl alcohol, stearyl alcohol, behenyl alcohol and cetostearyl alcohol. The most preferred is cetostearyl alcohol well known with its trade name Lanette O or as Lanette N in mixture with sodium cetearyl sulfate from Cognis.

The concentration of fatty alcohol(s) is in the range from 0.5 to 20%, preferably 1 to 15% by weight, calculated to total composition prior to mixing with oxidizing and bleaching and/or highlighting composition.

The third composition according to present invention comprises surfactants selected from anionic, nonionic, amphoteric (or zwitterionic) and/or cationic surfactants or their mixtures as emulsifier or solubilizer. Cationic surfactants are as well used as hair conditioners as mentioned above.

Anionic surfactants suitable within the scope of the invention are in principal known from the cleansing compositions These are anionic surfactants of the sulfate, sulfonate, carboxylate and alkyl phosphate type, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates.

Additional anionic surfactants useful within the scope of the invention are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof as well as alkyl amido polyether carboxylic acids and salts thereof. Such products have been known for some time and are on the market, for example, under the trade name "AKYPO®" and "AKYPO-SOFT®".

Further suitable anionic surfactants are also $C_8$-$C_{22}$-acyl aminocarboxylic acids or the water-soluble salts thereof. Especially preferred is N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

It is also possible to use mixtures of several anionic surfactants.

Further surfactants in the third composition according to the invention are nonionic surfactants which are one of the preferred emulsifying surfactant within the scope of present invention. Especially suited nonionic surfactants are, for example, long-chain fatty acid mono- and dialkanolamides, such as coco fatty acid mono- or diethanolamide and myristic fatty acid mono or diethanolamide, stearic acid mono or diethanolamide. Further nonionic surfactants suited are alkyl polyglucosides with an alkyl group of 8 to 18 carbon atoms, and with 1 to 5 glucoside units. Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics$^R$", as well as fatty alcohol ethoxylates. Further nonionic surfactants preferred in the dyeing compositions according to invention are $C_{10}$-$C_{22}$-fatty alcohol ethoxylates. Especially suited are $C_{10}$-$C_{22}$-fatty alcohol ethers, the alkyl polyglycol ethers known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16": The average degree of ethoxylation thereby ranges between about 2.5 and about 25, preferably about 10 and about 20.

As further surfactant component, the dyeing compositions according to the invention can also contain amphoteric or zwitterionic surfactants. Useful as such are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also proven suitable.

Cationic surfactants mentioned above as conditioner and especially those with single long alkyl chain such as cetrimonium chloride and behentrimonium chloride are also suitable emulsifiers according to present invention.

The concentration of one or more emulsifiers in the third compositions is in the range from 0.1 to 15%, preferably 0.5 to 10% by weight, calculated to total composition prior to mixing with oxidizing and bleaching and/or highlighting composition.

The third composition according to the present invention can contain organic solvent. Examples of such organic solvents are benzyloxy ethanol, benzyl alcohol, phenoxy ethanol, phenoxy isopropanol, methyl phenoxy ethanol, benzyl glycerol, N-benzyl formide, N-methyl pyrrolidone, N-ethyl pyrrolidone, cinnamyl alcohol, phenethyl alcohol, p-methyl benzyl alcohol, butyl cellosolve, methyl carbitol, ethyl carbitol, propyl carbitol, butyl carbitol, diethyleneglycol, diethyl ether and dipropyleneglycol diethyl ether. Typically the concentration of those solvents can be in the range from 0.5% to 10%, preferably 0.5-5% by weight calculated to the total composition prior to mixing with oxidizing and bleaching and/or highlighting composition.

The third composition can contain one or more thickening agents. The thickening agents disclosed for water free bleaching and/or highlighting compositions are also suitable for the third composition at the above given concentration ranges.

Another preferred compound in the composition of present invention especially in bleaching and/or highlighting composition and in the third composition is ceramide type of compounds according to general formula

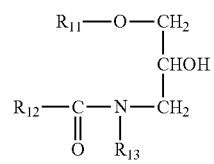

wherein $R_{11}$ and $R_{12}$ are independent from each other alkyl- or. alkenyl group with 10 to 22 carbon atoms, $R_{13}$ is alkyl or hydroxyl alkyl with 1 to 4 carbon atoms group and n is a number between 1 to 6, preferably 2 or 3. Preferred compound according to the above chemical structure is cetyl-PG-hydroxyethylpalmitamide. Concentration of ceramide type of compounds ranges from 0.01 to 2%, preferably 0.01 to 1% by weight calculated to total composition prior to mixing with oxidizing and bleaching and/or highlighting composition.

Another preferred compound in the composition of present invention especially in bleaching and/or highlighting composition and in the third composition is ubichinone type of compounds according to general formula

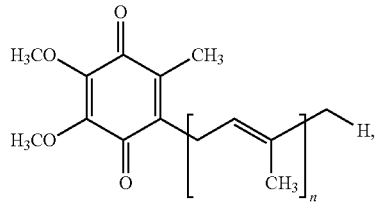

(IV)

wherein n is a number from 1 to 10. Concentration of ubichinone can vary between 0.001% and 10% by weight, calculated to the total composition prior to mixing with oxidizing and bleaching and/or highlighting composition.

The third composition may as well comprise UV filters of oil soluble, non-ionic, ones and/or as well those of water soluble and mainly of anionic character. Non-limiting examples are Benzophenone-1 Benzophenone-2, Benzophenone-3, Benzophenone-7, Benzophenone-6, Benzophenone-8, octylmethoxy cinnamate, homosalat to those of oil soluble ones and Benzophenone-4, benzophenone-9 to those anionic water soluble ones. It should be noted that the other UV filters of oil and water soluble ones should as well be possible to combine. Concentration of UV filters is in the range of 0.05 to 5%, preferably 0.1 to 2.5% and more preferably 0.1 to 1% by weight calculated to total composition prior to mixing with oxidizing and bleaching and/or highlighting composition.

Conditioning agents preferred are the ones mentioned above as oily lipophilic ingredients such as natural, synthetic and mineral oils and cationic compounds such as quaternary ammonium surfactants and cationic polymer disclosed above as well.

According to the preferred embodiment of the present invention, the thir composition comprises at least one direct dye. Suitable direct dyes are anionic, cationic and non-ionic nitro dyes.

Suitable anionic direct dyes in aqueous composition are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium. Among those, the most preferred anionic dyestuffs are Acid Red 52, DC Violet 2, DC Red 33, DC Orange 4, DC Red 27 and DC Yellow 10.

Suitable cationic dyes in aqueous composition are in principal those available on the market for cosmetic hair colouring applications. For this purpose, special reference is made to the PCT application WO 95/15144 of Ciba-Geigy AG. Some examples to those are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 76, Basic Violet 1, Basic Violet 2, Basic Violet 3, Basic Violet 10, Basic Violet 14, Basic Yellow 57, Basic red 51, Basic Yellow 87 and Basic Orange 31. The most preferred ones are Basic red 51, Basic Yellow 87 and Basic Orange 31 sold by CIBA.

Additionally, the aqueous compositions of the present invention may comprise neutral dyes (HC dyes), so called nitro dyes for shading purposes. Some examples to those are: HC Blue No.2, HC Blue No.4, HC Blue No.5, HC Blue No.6, HC Blue No.7, HC Blue No.8, HC Blue No.9, HC Blue No.10, HC Blue No.11, HC Blue No.12, HC Blue No.13, HC Brown No.1, HC Brown No.2, HC Green No.1, HC Orange No.1, HC Orange No.2, HC Orange No.3, HC Orange No.5, HC Red BN, HC Red No.1, HC Red No.3, HC Red No.7, HC Red No.8, HC Red No.9, HC Red No.10, HC Red No.11, HC Red No.13, HC Red No.54, HC Red No.14, HC Violet BS, HC Violet No.1, HC Violet No.2, HC Yellow No.2, HC Yellow No.4, HC Yellow No.5, HC Yellow No.6, HC Yellow No.7, HC Yellow No.8, HC Yellow No.9, HC Yellow No.10, HC Yellow No.11, HC Yellow No.12, HC Yellow No.13, HC Yellow No.14, HC Yellow No.15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Plant dyestuffs can also be used alone or in combination with synthetic direct-acting dyestuffs, for example henna (red or black), alkanna root, laccaic acid, indigo, logwood powder, madder root and rhubarb powder, etc.

From the above disclosed direct dyes the preferred are cationic and nitro dyes and most preferred are cationic direct dyes.

According to the invention, the third composition comprises one or more direct dye at a concentration of 0.1 to 7.5% by weight calculated to the total composition prior to mixing with bleaching and oxidizing compositions mentioned above. The third composition can also comprise mixture of several direct dyes i.e. an anionic, a cationic and/or a nonionic ones. In such a case the dyes may be mixed at any ratio with each other.

The above mentioned direct dyes of cationic, anionic and nonionic character can also be added into the water free bleaching and/or highlighting composition at the concentration given in the above paragraph. The direct dyes of different characters can certainly be mixed as well.

pH of the aqueous third composition of the present invention varies between 2 and 12, preferably 3-10, more preferably 4 to 8. pH is adjusted to the required pH by using monoethanolamine, triethanolamine, ammonia or its salts with acids such as ammonium chloride, ammonium sulphate, ammonium carbonate, ammonium bicarbonate, ammonium nitrate, or using alkaline solutions such as sodium hydroxide, potassium hydroxide and their respective salts with the known acids.

It should be noted that pH of the mixture of bleaching and/or highlighting composition, third composition and oxidizing lotion, ready to use composition, is in the range of 8 to 12, in particular between 9 and 11.

The mixing ratio of the bleaching and/or highlighting composition to third composition, depending on the colour result to be achieved varies between 10:1 to 1:1, preferably 8:1 to 2:1 and more preferably 5:1 to 3:1, all by weight, which may further mixed with an oxidizing lotion at a weight ratio of preferably 1:1. The above ratios are valid when third composition does not comprise direct dye. In case direct dye is contained in the third composition preferred mixing ratio is 1:1 which than mixed with oxidizing lotion.

Accordingly, further object of the present invention is a kit for bleaching and/or highlighting keratin fibres especially human hair comprising
 a—a water free composition comprising at least one compound with bleaching and/or highlighting effect and at least one calcium salt
 b—an aqueous composition comprising at least one oxidizing agent
 c—a third composition preferably an aqueous composition comprising at least one hair conditioning agent and/or a direct dye.

Further object of the present invention use of at least one calcium salt for preventing temperature increase above 40° C. preferably above 45° C. and more preferably 50° C. in a product in kit form comprising
 a—a water free composition comprising at least one compound with bleaching and/or highlighting effect
 b—an aqueous composition comprising at least one oxidizing agent
 c—a third composition preferably an aqueous composition comprising at least one hair conditioning agent
wherein calcium salt is preferably comprised in water free bleaching and/or highlighting composition.

Hair bleaching process is carried out as usual using the compositions of the present invention. Briefly, the mixture of water free composition, oxidizing lotion and optionally third compositions is prepared and applied onto dry hair and processed for 5 to 45 min and rinsed of from hair and shampooed, if necessary.

Although the preferred process for dyeing and bleaching is a single step process, two-step processes may as well be used with the compositions of the present invention.

One of the ways of carrying out in two steps is that in the first step, bleaching and/or highlighting composition of the present invention is firstly mixed with an oxidizing agent and applied onto hair and left 5 to 20 min and afterwards without rinsing off the third composition comprising at least one direct dye is applied onto hair and additionally processed for 5 to 30 min and rinsed off from hair and shampooed, if necessary.

In another way of carrying out the invention in two step is that in the first step, bleaching and/or highlighting composition of the present invention is firstly mixed with an oxidizing agent and applied onto hair and left 5 to 45 min and afterwards rinsed off from hair and subsequently in the second step dyeing composition is applied onto hair and additionally processed for 5 to 45 min and rinsed off from hair and shampooed, if necessary.

The composition of the present invention can contain additional ingredients such as preservatives, chelating agents, fragrance and substances customarily used in cosmetic bleaching and colouring compositions of keratin fibres, especially hair.

The invention is illustrated with the following examples, but not limited to.

EXAMPLE 1

Water Free Bleaching and/or Highlighting Compositions

| | |
|---|---|
| Potassium persulfate | 40 by weight |
| Sodium persulfate | 5 |
| Sodium carbonate | 1 |
| Sodium silicate | 10 |
| Diatomaceous Earth | 40 |
| Calcium sulfate | 4 |

The above composition is prepared by combining all powder components together and by mixing until homogeneity in a suitable mixer.

In order to test the excessive heat development preventing effect of calcium salt, in the example calcium sulphate, a comparative composition is prepared without 4% by weight calcium salt. In this case Diatomaceous Earth concentration is increased to 44% by weight. Both compositions were spiked with copper chloride at a concentration of 0.048 g per 100 g bleaching composition after mixing with oxidizing lotion below.

The water free bleaching compositions were mixed with an oxidizing composition of the following composition at a weight ratio of water free powder to oxidizing lotion 1:2.

Oxidizing Lotion

| | |
|---|---|
| Hydrogen peroxide | 9.00 (% by wt.) |
| Cetyl stearyl alcohol | 1.70 |
| Phosphoric acid | 0.50 |
| Sodium lauryl sulfate | 0.20 |
| Coenzyme Q10 | 0.05 |
| Cetyl PG hydroxyethyl palmitamide | 0.10 |
| Disodium hydrogen phosphate | 0.10 |
| Salicylic acid | 0.10 |
| Water | ad 100.00 |

The temperature of the mixture was followed for 60 min with a digital thermometer and recorded in regular distances. The results are presented in FIG. 1.

FIG. 1: Temperature changes of bleaching compositions

As clearly shown in FIG. 1 temperature of the composition without calcium sulphate increases to approximately 75° C. but temperature of the composition with calcium sulphate does not increase more than approximately 30° C. This results show clearly that in the presence of calcium chloride excessive heat development in bleaching compositions is prevented by the presence of calcium salt, in this particular example by the presence of calcium sulphate.

Similar results were observed with the following examples

EXAMPLE 2

Bleaching/Highlighting Powder Composition

| | |
|---|---|
| Hydroxyethylcellulose | 1.00% by weight |
| Cellulose gum | 3.00 |
| Tetrasodium EDTA | 2.00 |
| Sodium carbonate | 1.00 |
| Ammonium persulfate | 21.00 |
| Potassium persulfate | 46.60 |
| Sodium metasilicate | 10.00 |
| Diatomaceous Earth | 11.00 |
| Polyquaternium - 10 | 0.50 |
| Calcium chloride | 3.00 |

The above composition was tested in a half side test for its performance on bleaching with 10 volunteers having shoulder length hair. As a comparative composition a composition without calcium chloride but with 14% by weight diatomaceous earth was prepared. Bleaching composition was prepared by mixing above water free composition with oxidizing lotion of example 1 at a weight ratio of 1:2 (powder to lotion). Approximately 30 g of each was applied onto hair and processed for 30 min at ambient temperature. Afterwards bleaching composition was rinsed off from hair and shampooed ones and dried with a hair drier.

It was observed that the half side bleached with a composition according to present invention was better in combing, softer and had more shine. Volunteers were of the opinion that it was more natural upon touching than the half side bleached with comparative composition.

In a further test, temperature of both compositions was observed after spiking with copper chloride at a concentration of 0.048 g per 100 g bleaching composition. It was observed that the temperature of the comparative composition was reached approximately 83° C. whereas the temperature of the inventive compositions did not go beyond 32° C.

EXAMPLE 3

Bleaching and colouring in a single process was carried our using the bleaching composition of example 1, dyeing composition according to the composition below and an oxidizing lotion composition of example 1, however with 6% hydrogen peroxide content instead of 9%.

The Third Composition with Dyestuff

|  | % by weight |
| --- | --- |
| Cocamide MEA | 4.00 |
| Cetearyl alcohol | 10.00 |
| Tegin P | 1.40 |
| Propylene Glycol | 2.40 |
| Oleic acid | 3.00 |
| Coenzyme Q10 | 0.10 |
| Ammonium chloride | 0.50 |
| Tetrasodium EDTA | 0.20 |
| Sodium lauryl sulfate | 1.50 |
| Polysilicone-9 | 0.20 |
| Pentaphenyl trimethyl trisiloxane | 5.00 |
| Cetyl PG hydroxyethyl palmitamide | 0.10 |
| Basic red 51 | 0.50 |
| Water | to 100 |

The bleaching composition of example 2, dyeing composition of above and oxidizing lotion of example 1 were mixed at a weight ratio of 1:1:1 and was applied onto parts of hair (streak) and left 30 min at 40° C. and rinsed off with water and shampooed. Intensive highlighted red streaks were obtained.

Similar results were observed when other cationic, anionic and/or nonionic nitro dyes mentioned in the description are used instead of the cationic dye in the example.

EXAMPLE 4

The Third Composition

| Cetrimonium chloride | 1.0 |
| --- | --- |
| Hydroxyethylcellulose | 1.0 |
| Cetearyl alcohol | 5.0 |
| Hydrolysed silk | 1.0 |
| Fragrance | q.s. |
| Preservative | q.s. |
| Citric acid | q.s. to pH 5.0 |
| Water | to 100 |

Water free bleaching composition of example 2 is mixed with above composition and with oxidizing lotion of example 1 at a weight ratio of 1:1.9:0.1 (water free composition: oxidizing lotion: the third composition). The resulting composition was tested against a bleaching composition of Example 2. It was observed that the half side bleached with a composition mixed with third composition is much more cared interms of combability, shine and softness.

EXAMPLE 5

Bleaching/Highlighting Powder Composition

| Hydroxyethylcellulose | 1.40% by weight |
| --- | --- |
| Cellulose gum | 3.20 |
| Xanthan gum | 0.30 |
| Tetrasodium EDTA | 2.00 |
| Sodium carbonate | 1.00 |
| Ammonium persulfate | 21.00 |
| Potassium persulfate | 46.60 |
| Sodium metasilicate | 10.20 |
| Corn starch | 1.10 |
| Diatomaceous Earth | 9.30 |
| Calcium sulphate | 2.80 |
| Polyquaternium - 10 | 0.10 |
| Silica* | 1.00 |
| Synthetic fluorphologopite** | 1.00 |

*Aerosil 380
**Synthetic fluorphologopite used is commercially available from Merck with a particle size distribution in the range of 5 to 45 μm.

The above composition was produced in the same way as in example 1 and also used in the same way as described under Example 1. Similar results were obtained in the temperature test. When tested against a composition without calcium sulphate it was found our hair felt less damaged upon touching which was supported by better combability, better shine and softer feel.

The invention claimed is:

1. A method for preventing excessive heat development during bleaching and/or highlighting of keratin fibers, comprising the steps of: incorporating 0.1 to 20% by weight, calculated to the total composition prior to mixing, of at least one calcium salt in a bleaching and/or highlighting composition, and applying said composition to the keratin fibers to achieve bleaching and/or highlighting without excessive heat development, wherein the bleaching and/or highlighting composition comprised between 30 to 80 wt. %, calculated to the total composition, of a persulfate compound, and wherein the bleaching composition is water-free and in powder form.

2. The method of claim 1, further comprising mixing the bleaching and/or highlighting composition with an oxidizing composition, whereby the temperature does not increase above 40° C. in a period of at least 60 min after said mixing.

3. The method according to claim 1, wherein at least one calcium salt is selected from a group consisting of calcium aluminium borosilicate, calcium aspartate, calcium benzoate, calcium acetate, calcium carbonate, calcium citrate, calcium dihydrogen phosphate, calcium fluoride, calcium hydroxide, calcium lactate, calcium monofluorophosphate, calcium oxide, calcium phosphate, calcium propionate, calcium pyrophosphate, calcium sulphate, calcium nitrate, calcium salicylate, calcium silicate, hydrate, calcium tartarate, tricalcium phosphate, calcium chloride, calcium iodide and calcium bromide.

4. The method according to claim 2, wherein the composition comprises at least one compound with bleaching effect at a concentration of 5% by weight, calculated to total composition prior to mixing with oxidizing composition.

5. The method according to claim 2, wherein the composition comprises at least one ammonium salt.

6. The method according to claim 2, wherein the composition comprises silicone oil and/or mineral oil and/or natural oil as lipophilic ingredient.

7. The method according to claim 2, wherein the composition comprises polymer.

8. The method according to claim 2, wherein the composition comprises additionally at least one lipophilic ingredient at a concentration of 1 to 50% by weight calculated to total composition prior to mixing with oxidizing lotion.

9. The method according to claim 1, wherein the composition comprises additionally at least one lipophilic ingredient at a concentration of 1 to 50% by weight calculated to total composition prior to mixing with oxidizing lotion.

10. The method according to claim 1 wherein the bleaching composition comprises between 40 to 70 wt. %, calculated to the total composition, of a persulfate compound.

11. The method according to claim 1 wherein the persulfate compound is selected from the group consisting of sodium persulfate, potassium persulfate and ammonium persulfate.

12. The method according to claim 11 wherein the persulfate compound is potassium persulfate.

* * * * *